(12) United States Patent
Gonzalez-Hernandez

(10) Patent No.: US 9,254,154 B2
(45) Date of Patent: Feb. 9, 2016

(54) ANTERIOR LESSER TUBEROSITY FIXED ANGLE FIXATION DEVICE AND METHOD OF USE ASSOCIATED THEREWITH

(75) Inventor: Eduardo Gonzalez-Hernandez, Coconut Grove, FL (US)

(73) Assignee: TOBY ORTHOPAEDIC, INC., Miami, FL (US)

( * ) Notice: Subject to any disclaimer, the term of this patent is extended or adjusted under 35 U.S.C. 154(b) by 36 days.

(21) Appl. No.: 13/412,039

(22) Filed: Mar. 5, 2012

(65) Prior Publication Data

US 2012/0226323 A1   Sep. 6, 2012

Related U.S. Application Data

(60) Provisional application No. 61/449,012, filed on Mar. 3, 2011.

(51) Int. Cl.
*A61B 17/80* (2006.01)
(52) U.S. Cl.
CPC .................................. *A61B 17/8061* (2013.01)
(58) Field of Classification Search
CPC .................................................... A61B 17/8061
USPC ......................................................... 606/286
See application file for complete search history.

(56) References Cited

U.S. PATENT DOCUMENTS

| | | |
|---|---|---|
| 1,950,799 A | 3/1934 | Jones |
| 2,500,370 A | 3/1950 | McKibbin |
| 2,555,291 A | 5/1951 | Poupitch |
| 2,682,265 A | 6/1954 | Collison |
| 2,853,114 A | 9/1958 | Barry |
| 2,875,663 A | 3/1959 | Wieber |
| 3,489,143 A | 1/1970 | Halloran |
| 3,552,389 A | 1/1971 | Allgower et al. |
| 3,579,831 A | 5/1971 | Stevens et al. |
| 3,716,050 A | 2/1973 | Johnston |
| 3,791,380 A | 2/1974 | Dawidowski |
| 3,900,025 A | 8/1975 | Barnes, Jr. |
| 4,263,904 A | 4/1981 | Judet |
| 4,535,768 A | 8/1985 | Hourahane et al. |
| 4,683,878 A | 8/1987 | Carter |
| 4,733,654 A | 3/1988 | Marino |
| 4,776,330 A | 10/1988 | Chapman et al. |
| 4,790,302 A | 12/1988 | Colwill et al. |

(Continued)

FOREIGN PATENT DOCUMENTS

| | | |
|---|---|---|
| DE | 86 28 766 U1 | 12/1986 |
| DE | 89 07 443 U1 | 9/1989 |

(Continued)

OTHER PUBLICATIONS

U.S. Appl. No. 10/993,723, filed Nov. 2004, Gonzalez-Hernandez.

(Continued)

*Primary Examiner* — David Bates
(74) *Attorney, Agent, or Firm* — Martin & Ferraro, LLP

(57) ABSTRACT

A fixation device serves in facilitating reduction and repair of a fractured humerus. The fixation device includes a bone plate adapted to overlie and contact portions of a proximal humerus and a humeral shaft. The bone plate includes at least a body portion overlying the humeral shaft, and an end portion overlying a portion of the proximal humerus. The end portion can facilitate attachment of the bone plate to the lesser tuberosity of the proximal humerus.

14 Claims, 5 Drawing Sheets

(56) References Cited

U.S. PATENT DOCUMENTS

| | | |
|---|---|---|
| 4,794,919 A | 1/1989 | Nilsson |
| 4,796,612 A | 1/1989 | Reese |
| 4,838,264 A | 6/1989 | Bremer et al. |
| 4,858,602 A | 8/1989 | Seidel et al. |
| 4,870,957 A | 10/1989 | Goble et al. |
| 5,003,969 A | 4/1991 | Azer et al. |
| 5,015,248 A | 5/1991 | Burstein et al. |
| 5,041,113 A | 8/1991 | Biedermann et al. |
| 5,041,114 A | 8/1991 | Chapman et al. |
| 5,180,383 A | 1/1993 | Haydon |
| 5,190,544 A | 3/1993 | Chapman et al. |
| 5,324,291 A | 6/1994 | Ries et al. |
| 5,356,410 A | 10/1994 | Pennig |
| 5,364,399 A | 11/1994 | Lowery et al. |
| 5,423,860 A | 6/1995 | Lizardi et al. |
| 5,437,667 A | 8/1995 | Papierski et al. |
| 5,443,516 A | 8/1995 | Albrektsson et al. |
| 5,458,654 A | 10/1995 | Tepic |
| 5,462,547 A | 10/1995 | Weigum |
| 5,472,444 A | 12/1995 | Huebner et al. |
| 5,505,734 A | 4/1996 | Caniggia et al. |
| 5,578,035 A | 11/1996 | Lin |
| 5,584,835 A | 12/1996 | Greenfield |
| 5,586,985 A | 12/1996 | Putnam et al. |
| 5,601,553 A | 2/1997 | Trebing et al. |
| 5,620,449 A | 4/1997 | Faccioli et al. |
| 5,658,287 A | 8/1997 | Hofmann et al. |
| 5,665,088 A | 9/1997 | Gil et al. |
| 5,674,222 A | 10/1997 | Berger et al. |
| 5,676,667 A | 10/1997 | Hausman |
| 5,681,311 A | 10/1997 | Foley et al. |
| 5,709,686 A | 1/1998 | Talos et al. |
| 5,749,872 A | 5/1998 | Kyle et al. |
| 5,766,174 A | 6/1998 | Perry |
| 5,776,194 A | 7/1998 | Mikol et al. |
| 5,779,704 A | 7/1998 | Kim |
| 5,785,712 A | 7/1998 | Runciman et al. |
| 5,840,078 A | 11/1998 | Yerys |
| 5,868,749 A | 2/1999 | Reed |
| 5,931,839 A | 8/1999 | Medoff |
| 5,976,139 A | 11/1999 | Bramlet |
| 5,980,575 A | 11/1999 | Albrektsson et al. |
| 6,030,389 A | 2/2000 | Wagner et al. |
| 6,096,040 A * | 8/2000 | Esser ............... A61B 17/8061 606/280 |
| 6,149,653 A | 11/2000 | Deslauriers |
| 6,152,927 A | 11/2000 | Farris et al. |
| 6,200,330 B1 | 3/2001 | Benderev et al. |
| 6,206,881 B1 | 3/2001 | Frigg et al. |
| D443,060 S | 5/2001 | Benirschke et al. |
| 6,270,499 B1 | 8/2001 | Leu et al. |
| D449,692 S | 10/2001 | Michelson |
| 6,302,887 B1 | 10/2001 | Spranza et al. |
| 6,331,179 B1 | 12/2001 | Freid et al. |
| 6,348,052 B1 | 2/2002 | Sammarco |
| 6,358,250 B1 | 3/2002 | Orbay |
| 6,364,881 B1 | 4/2002 | Apgar et al. |
| 6,364,882 B1 | 4/2002 | Orbay |
| 6,379,359 B1 | 4/2002 | Dahners |
| 6,398,783 B1 | 6/2002 | Michelson |
| 6,406,478 B1 | 6/2002 | Kuo |
| 6,409,768 B1 | 6/2002 | Tepic et al. |
| 6,413,259 B1 | 7/2002 | Lyons et al. |
| 6,440,135 B2 | 8/2002 | Orbay et al. |
| 6,468,278 B1 | 10/2002 | Muckter |
| 6,572,620 B1 | 6/2003 | Schon et al. |
| 6,620,195 B2 | 9/2003 | Goble et al. |
| 6,623,486 B1 | 9/2003 | Weaver et al. |
| 6,663,669 B1 | 12/2003 | Reiley |
| 6,669,701 B2 | 12/2003 | Steiner et al. |
| 6,695,844 B2 | 2/2004 | Bramlet et al. |
| 6,706,046 B2 | 3/2004 | Orbay et al. |
| 6,712,820 B2 | 3/2004 | Orbay |
| 6,719,759 B2 | 4/2004 | Wagner et al. |
| 6,730,090 B2 | 5/2004 | Orbay et al. |
| 6,776,781 B1 | 8/2004 | Uwaydah |
| 6,863,671 B1 | 3/2005 | Strobel et al. |
| 6,866,665 B2 | 3/2005 | Orbay |
| 6,916,323 B2 | 7/2005 | Kitchens |
| 6,945,973 B2 | 9/2005 | Bray |
| 7,001,388 B2 | 2/2006 | Orbay et al. |
| 7,063,701 B2 | 6/2006 | Michelson |
| 7,128,744 B2 | 10/2006 | Weaver et al. |
| D536,453 S | 2/2007 | Young et al. |
| 7,220,246 B2 | 5/2007 | Raulerson |
| 7,229,445 B2 | 6/2007 | Hayeck et al. |
| 7,235,079 B2 | 6/2007 | Jensen et al. |
| 7,354,441 B2 | 4/2008 | Frigg |
| 7,500,983 B1 | 3/2009 | Kaiser et al. |
| 7,563,263 B2 | 7/2009 | Orbay et al. |
| 7,582,107 B2 | 9/2009 | Trail et al. |
| 7,591,823 B2 | 9/2009 | Tipirneni |
| 7,604,657 B2 | 10/2009 | Orbay et al. |
| 7,637,908 B1 | 12/2009 | Gonzalez-Hernandez |
| 7,651,517 B2 | 1/2010 | Konieczynski et al. |
| 7,655,029 B2 | 2/2010 | Niederberger et al. |
| 7,695,472 B2 | 4/2010 | Young |
| 7,722,653 B2 | 5/2010 | Young et al. |
| 7,740,648 B2 | 6/2010 | Young et al. |
| 7,744,638 B2 | 6/2010 | Orbay |
| 7,776,076 B2 | 8/2010 | Grady, Jr. et al. |
| 7,780,667 B2 | 8/2010 | Watanabe et al. |
| 7,780,710 B2 | 8/2010 | Orbay et al. |
| 7,896,886 B2 | 3/2011 | Orbay et al. |
| 7,909,859 B2 | 3/2011 | Mosca et al. |
| 7,914,532 B2 | 3/2011 | Shaver et al. |
| 7,927,341 B2 | 4/2011 | Orbay et al. |
| 7,938,850 B2 | 5/2011 | Orbay et al. |
| 7,951,176 B2 | 5/2011 | Grady et al. |
| 7,951,178 B2 | 5/2011 | Jensen |
| 7,955,364 B2 | 6/2011 | Ziolo et al. |
| D643,121 S | 8/2011 | Milford et al. |
| 8,021,402 B2 | 9/2011 | Martin et al. |
| D646,785 S | 10/2011 | Milford |
| 8,062,296 B2 | 11/2011 | Orbay et al. |
| 8,062,367 B2 | 11/2011 | Kirschman |
| 8,100,953 B2 | 1/2012 | White et al. |
| 8,182,485 B1 | 5/2012 | Gonzalez-Hernandez |
| 8,317,842 B2 | 11/2012 | Graham et al. |
| 8,523,902 B2 | 9/2013 | Heaven et al. |
| 8,574,234 B2 | 11/2013 | Gonzalez-Hernandez |
| 8,597,363 B2 | 12/2013 | Liverneaux et al. |
| 8,690,916 B2 | 4/2014 | Gonzalez-Hernandez |
| 8,728,126 B2 | 5/2014 | Steffen |
| 8,764,808 B2 | 7/2014 | Gonzalez-Hernandez |
| 8,961,573 B2 | 2/2015 | Gonzalez-Hernandez |
| 2002/0091391 A1 | 7/2002 | Cole et al. |
| 2003/0135212 A1 | 7/2003 | Chow |
| 2003/0135216 A1 | 7/2003 | Sevrain |
| 2003/0208210 A1 | 11/2003 | Dreyfuss et al. |
| 2004/0097939 A1 | 5/2004 | Bonutti |
| 2004/0193278 A1 | 9/2004 | Maroney et al. |
| 2004/0210220 A1 * | 10/2004 | Tornier ............... 606/69 |
| 2005/0004574 A1 | 1/2005 | Muckter |
| 2005/0015089 A1 | 1/2005 | Young et al. |
| 2005/0021033 A1 | 1/2005 | Zeiler et al. |
| 2005/0038513 A1 | 2/2005 | Michelson |
| 2005/0085819 A1 | 4/2005 | Ellis et al. |
| 2005/0182405 A1 | 8/2005 | Orbay et al. |
| 2005/0240187 A1 | 10/2005 | Huebner et al. |
| 2005/0267476 A1 | 12/2005 | Chervitz et al. |
| 2005/0288681 A1 | 12/2005 | Klotz et al. |
| 2006/0015072 A1 | 1/2006 | Raulerson |
| 2006/0015101 A1 | 1/2006 | Warburton et al. |
| 2006/0106385 A1 | 5/2006 | Pennig |
| 2006/0161156 A1 | 7/2006 | Orbay |
| 2006/0217722 A1 | 9/2006 | Dutoit et al. |
| 2006/0229623 A1 | 10/2006 | Bonutti et al. |
| 2006/0235400 A1 | 10/2006 | Scheider |
| 2006/0241617 A1 | 10/2006 | Holloway et al. |
| 2006/0264947 A1 | 11/2006 | Orbay et al. |
| 2006/0264956 A1 | 11/2006 | Orbay et al. |
| 2006/0271105 A1 | 11/2006 | Foerster et al. |
| 2007/0005074 A1 | 1/2007 | Chudik |

(56) References Cited

U.S. PATENT DOCUMENTS

| | | |
|---|---|---|
| 2007/0016205 A1 | 1/2007 | Beutter et al. |
| 2007/0083207 A1 | 4/2007 | Ziolo et al. |
| 2007/0123880 A1 | 5/2007 | Medoff |
| 2007/0123885 A1 | 5/2007 | Kirschman |
| 2007/0162015 A1 | 7/2007 | Winquist et al. |
| 2007/0167953 A1 | 7/2007 | Prien et al. |
| 2007/0233114 A1 | 10/2007 | Bouman |
| 2007/0233115 A1 | 10/2007 | Sixto et al. |
| 2008/0015593 A1 | 1/2008 | Pfefferle et al. |
| 2008/0045960 A1 | 2/2008 | Bruecker et al. |
| 2008/0119895 A1* | 5/2008 | Manceau ............ A61B 17/8042 606/280 |
| 2008/0132955 A1 | 6/2008 | Frigg |
| 2008/0140130 A1 | 6/2008 | Chan et al. |
| 2008/0154311 A1 | 6/2008 | Staeubli |
| 2008/0161853 A1 | 7/2008 | Arnold et al. |
| 2008/0161860 A1 | 7/2008 | Ahrens et al. |
| 2008/0161863 A1 | 7/2008 | Arnold et al. |
| 2008/0221577 A1 | 9/2008 | Elghazaly |
| 2008/0234749 A1 | 9/2008 | Forstein |
| 2008/0234752 A1 | 9/2008 | Dahners |
| 2008/0249572 A1 | 10/2008 | Tandon |
| 2009/0012571 A1 | 1/2009 | Perrow et al. |
| 2009/0024173 A1 | 1/2009 | Reis, Jr. |
| 2009/0048681 A1 | 2/2009 | Vlachos |
| 2009/0069851 A1* | 3/2009 | Gillard ............... A61B 17/1684 606/280 |
| 2009/0076554 A1 | 3/2009 | Huebner et al. |
| 2009/0105838 A1 | 4/2009 | Russo et al. |
| 2009/0125070 A1 | 5/2009 | Sixto, Jr. et al. |
| 2009/0171399 A1 | 7/2009 | White et al. |
| 2009/0192550 A1 | 7/2009 | Leung et al. |
| 2009/0216270 A1 | 8/2009 | Humphrey |
| 2009/0228010 A1 | 9/2009 | Gonzalez-Hernandez et al. |
| 2009/0254089 A1 | 10/2009 | Tipirneni et al. |
| 2009/0254189 A1 | 10/2009 | Scheker |
| 2009/0264936 A1 | 10/2009 | Gonzalez-Hernandez |
| 2009/0275987 A1 | 11/2009 | Graham et al. |
| 2009/0275991 A1 | 11/2009 | Medoff |
| 2009/0281577 A1 | 11/2009 | Graham et al. |
| 2009/0281579 A1 | 11/2009 | Spencer |
| 2009/0299369 A1 | 12/2009 | Orbay et al. |
| 2009/0306711 A1 | 12/2009 | Stone et al. |
| 2009/0312758 A1* | 12/2009 | Petit et al. ............... A61B 17/74 606/60 |
| 2009/0312760 A1 | 12/2009 | Forstein et al. |
| 2009/0312802 A1 | 12/2009 | Dasilva |
| 2009/0326591 A1 | 12/2009 | Spencer, Jr. |
| 2010/0030276 A1 | 2/2010 | Huebner et al. |
| 2010/0057086 A1 | 3/2010 | Price et al. |
| 2010/0145339 A1 | 6/2010 | Steffen |
| 2010/0145397 A1 | 6/2010 | Overes et al. |
| 2010/0198258 A1 | 8/2010 | Heaven et al. |
| 2010/0217393 A1 | 8/2010 | Theofilos |
| 2010/0262194 A1 | 10/2010 | Wagner et al. |
| 2010/0274245 A1 | 10/2010 | Gonzalez-Hernandez |
| 2010/0324602 A1 | 12/2010 | Huebner et al. |
| 2010/0331844 A1 | 12/2010 | Ellis et al. |
| 2011/0152943 A1 | 6/2011 | Gonzalez-Hernandez |
| 2011/0160730 A1 | 6/2011 | Schonhardt et al. |
| 2012/0083848 A1 | 4/2012 | Gonzalez-Hernandez |
| 2012/0109322 A1* | 5/2012 | Gonzalez-Hernandez A61B 17/80 623/19.14 |
| 2012/0197305 A1 | 8/2012 | Gonzalez-Hernandez |
| 2012/0197308 A1 | 8/2012 | Gonzalez-Hernandez |
| 2012/0226321 A1 | 9/2012 | Gonzalez-Hernandez |
| 2012/0226322 A1 | 9/2012 | Gonzalez-Hernandez |
| 2013/0096629 A1 | 4/2013 | Rollinghoff et al. |
| 2013/0116734 A1 | 5/2013 | Gonzalez-Hernandez |
| 2013/0338780 A1 | 12/2013 | Berchoux et al. |
| 2014/0121709 A1 | 5/2014 | Gonzalez-Hernandez |
| 2014/0121779 A1 | 5/2014 | Gonzalez-Hernandez |
| 2014/0172020 A1 | 6/2014 | Gonzalez-Hernandez |
| 2014/0180344 A1 | 6/2014 | Gonzalez-Hernandez |
| 2014/0277177 A1 | 9/2014 | Gonzalez-Hernandez |
| 2015/0045898 A1 | 2/2015 | Gonzalez-Hernandez |
| 2015/0164566 A1 | 6/2015 | Gonzalez-Hernandez |

FOREIGN PATENT DOCUMENTS

| | | |
|---|---|---|
| DE | 43 43 117 A1 | 6/1995 |
| DE | 198 57 279 A1 | 6/2000 |
| DE | 299 07 161 U1 | 8/2000 |
| EP | 0 551 588 A1 | 11/1992 |
| EP | 1 132 052 A2 | 9/2001 |
| EP | 1 468 655 A2 | 10/2004 |
| FR | 2 606 268 A1 | 5/1988 |
| FR | 2 680 673 A1 | 3/1993 |
| FR | 2 712 173 A1 | 5/1995 |
| JP | 4-138152 A | 5/1992 |
| WO | WO 99/38448 A1 | 8/1999 |
| WO | WO 02/071963 A1 | 9/2002 |
| WO | WO 2005/037117 A1 | 4/2005 |
| WO | WO 2008/007194 A2 | 1/2008 |
| WO | WO 2008/007196 A2 | 1/2008 |
| WO | WO 2012/003884 | 1/2012 |

OTHER PUBLICATIONS

U.S. Appl. No. 11/050,304, filed Feb. 2005, Gonzalez-Hernandez.
U.S. Appl. No. 11/079,350, filed Mar. 2005, Gonzalez-Hernandez.
U.S. Appl. No. 11/366,676, filed Mar. 2006, Gonzalez-Hernandez.
U.S. Appl. No. 11/493,122, filed Jul. 2006, Gonzalez-Hernandez.
U.S. Appl. No. 11/526,331, filed Sep. 2006, Gonzalez-Hernandez.
U.S. Appl. No. 11/707,775, filed Feb. 2007, Gonzalez-Hernandez.
U.S. Appl. No. 13/253,564, filed Oct. 2011, Gonzalez-Hernandez.
U.S. Appl. No. 13/282,810, filed Oct. 2011, Gonzalez-Hernandez.
U.S. Appl. No. 13/411,069, filed Mar. 2012, Gonzalez-Hernandez.
U.S. Appl. No. 13/411,100, filed Mar. 2012, Gonzalez-Hernandez.
Acumed; ACU-LOC Wrist Plating System; Jul. 2009; 20 pages.
Acumed; The Mayo Clinic Congruent Elbow Plates (catalog); 2003; 19 pages.
Acumed, The Mayo Clinic Congruent Elbow Plate System (catalog): Apr. 2006; 20 pages.
Christie, J., C.R. Howie and P.C. Armour, Fixation of displaced subcapital femoral fractures. Compression screw fixation versus double divergent pins. J Bone Joint Surg [Br] 1988; 70-B: 199-201.
Cross, W.M. et al., "Achieving stable fixation: biomechanical designs for fracture healing," AAOS Now (2008) 3 pages.
Guha, AR, et al.; "A New Technique of Fixation of Radial Head Fractures Using a Modified Tubular Plate," Journal of Postgraduate Medicine; Jul. 2004; vol. 50, Issue 2; pp. 113-114; Accessed Aug. 6, 2008 at: http://www.jpgmonline.com/article.asp?issn=0022-3859;year=2004;volume=50;issue=2;spage=113;epage=114;aulast=Guha.
Hand innovations, LLC; DVR Anatomic, Volar Plating System; 2007; 4 pages.
Hussain M., R.N. Natarajan, A.H. Fayyazi, B.R. Braaksma, G.B. Andersson and H.S. An, Screw angulation affects bone-screw stresses and bone graft laod sharing in an anterior cervical corpectomy fusion with a rigid screw-plate construct: a finite element model study; Spine Journal, vol. 9, Issue 12, Dec. 2008; pp. 1016-1023 (published online Oct. 12, 2009).
Lakatos, R. et al.; "General principles of internal fixation"; eMedicine; Aug. 2006; 51 pages.
"MIS Technique," published by Zimmer®, 1 page (undated).
Robert, III, K.Q., R. Chandler, R,V, Barratta, K.A. Thomas and M.V. Harris, The effect of divergent screw placement on the intial strength of plate-to-bone fixiation. J Trauma. Dec. 2003;55(6):1139-44.
Synthes; 3.5 mm LCP Periarticular Humerus Plate; Apr. 2010; 22 pages.
Synthes; Locking Compression Plate (LCP) System (brochure); 2003; 6 pages.
Synthes; Locking Compression Plate (LCP) System (brochure); Jan. 2007; 6 pages.
Written Opinion of the International Searching Authority; International Application No. PCT/2009/036211; Sep. 23, 2010; 8 pages.
"Zimmer® Universal Looking System," The Journal of Bone and Joint Surgery, vol. 39, No. 7, Jul. 2007, 1 page.

(56) References Cited

OTHER PUBLICATIONS

Zimmer, Inc.; "Zimmer Universal Locking System;" brochure; 2009, 2 pages.
Zimmer, Inc. "Zimmer Holdings to Launch Innovative Locking Plate System at Orthopaedic Trauma Association Meeting," Sep. 14, 2006; 3 pages.
Zimmer, Inc.; "Zimmer Small Fragment Universal Locking System;" Surgical Technique; 2010; 16 pages.
Zimmer; Zimmer Periarticular Plating System-Low-Profile Fixation (catalog); 2003; 8 pages.
Postak, Paul D.; "Biomechanical Properties of Fixed-Angle Volar Distal Radius Plates Under Dynamic Loading;" 2007; 6 pages.
Synthes, "Large Fragment LCP Instrument and Implant Set;" technique guide; 2003; 31 pages.
Synthes, "Locking Compression Plate (LCP) System. Locking screw technology and conventional plating in one system;" 2003; 6 pages.
Synthes; Modular Mini Fragment LCP System (brochure); 2007; 12 pages.
Synthes; Small Fragment Locking Compression Plate (LCP) System (brochure); 2002; 43 pages.
Zimmer, Inc. "Zimmer® Universal Locking System," brochure (2006), 4 pages.
U.S. Appl. No. 13/840,194, filed Mar. 2013, Gonzalez-Hernandez.
U.S. Appl. No. 14/189,681, filed Feb. 2014, Gonzalez-Hernandez.
U.S. Appl. No. 14/213,310, filed Mar. 2014, Gonzalez-Hernandez.

* cited by examiner

ANTERIOR LESSER TUBEROSITY FIXED ANGLE FIXATION DEVICE AND METHOD OF USE ASSOCIATED THEREWITH

The present application claims the benefit of provisional Application No. 61/449,012, filed Mar. 3, 2011; which is incorporated by reference herein.

BACKGROUND OF THE INVENTION

1. Field of the Invention

The present invention generally relates to a fixation device used to facilitate reduction and repair of a fractured bone. More particularly, the present invention relates to a bone plate for creating a mechanically stronger connection between the bone plate and portions of a fractured humerus including the proximal humerus and the humeral shaft. More specifically, the present invention relates to a bone plate configured to provide optimal angles for bone screws received therethrough to decrease the incidence of penetration of the bone screws through the articular surface of the humeral head.

2. Description of the Prior Art

Current state of the art in surgical fracture fixation of the proximal humerus requires the application of a bone plate to the greater tuberosity of the proximal humerus. To attach the bone plate to the proximal humerus, bone screws (threadably or non-threadably engaging the bone plate) are inserted through the bone plate into the proximal humerus. In attaching the bone plate to the proximal humerus, the bone screws are ultimately received under the surface of the humeral head.

The bone screws used to attach the bone plate to the proximal humerus will likely be disposed at a significantly perpendicular angle with respect to the articular surface of the humeral head. This attachment orientation provides insufficient mechanical strength to maintain rigid attachment of the bone plate to the proximal humerus when subjected to joint reaction forces. As such, there remains a significant incidence of loss of fracture reduction and fracture fixation. In order to maximize stability of the connection, it is necessary to utilize long bone screws, so as to maximize the purchase thereof. However, given the significantly perpendicular angle of the bone screws relative to the articular surface, if there is any collapse or subsidence of the humeral head relative to the bone plate, the tips of the bone screws will penetrate the articular surface. Accordingly, there also remains a significant incidence of joint penetration.

Therefore, there is a need for a fixation device and method of use associated therewith that provides more optimal screw angles with respect to the articular surface of the humeral head and a mechanically stronger connection between the bone plate and the humerus. Such a fixation device can insure that bone screws are disposed at varying angles that are more tangential to the articular surface to prevent loss of fracture fixation and fracture reduction, and/or prevent penetration of the bone screws through the articular surface of the humeral head.

SUMMARY OF THE INVENTION

The present invention in a preferred embodiment contemplates a fixation device for facilitating reductions and repair of a fractured humerus, the fixation device including a bone plate adapted to overlie and contact portions of a proximal humerus and a humeral shaft, the bone plate having a body portion, a neck portion, and a first end portion, the body portion including a first end, a second end opposite the first end, a longitudinal axis extending between the first and second ends, a plurality of bone screw receiving apertures adapted to overlie the humeral shaft, and a first contact surface adapted to contact the exterior surface of the humeral shaft, the longitudinal axis of the body portion being adapted to be substantially aligned with the humeral shaft when the bone plate is attached to the humerus, the neck portion extending from the body portion, the neck portion being adapted to bridge the biceps groove of the proximal humerus when the bone plate is attached to the humerus, the first end portion being contiguous to the neck portion, the first end portion including a second contact surface adapted to contact the exterior surface of the lesser tuberosity of the proximal humerus, and at least two bone screw receiving apertures adapted to overlie the lesser tuberosity, the at least two bone screw receiving apertures each including an axis, the axes of the at least two bone receiving apertures being oriented away from the articular surface of the proximal humerus when the bone plate is attached to the humerus; at least a first set of bone screws, a first bone screw of the first set of bone screws being received through a first of the plurality of bone screw receiving apertures and into the humeral shaft, and a second bone screw of the first set of bone screws being received through a second of the plurality of bone screw receiving apertures and into the humeral shaft, the first and second bone screws of the first set of bone screws facilitating attached of the bone portion to the humeral shaft; and at least a second set of bone screws, each bone screw of the at least a second set of bone screws having a longitudinal axis, a first bone screw of the second set of bone screws being received through a first of the at least two bone screw receiving apertures and into the lessor tuberosity, a second bone screw of the second set of bone screws being received through a second of the at least two bone screw receiving apertures and into the lessor tuberosity, the longitudinal axes of the first and second bone screws of the second set of bone screws being aligned with the axes of the first and second bone screw receiving apertures and being oriented away from the articular surface of the proximal humerus when the bone plate is attached to the humerus.

The present invention in a further preferred embodiment contemplates A fixation device for facilitating reductions and repair of a fractured humerus, the fixation device including a bone plate adapted to overlie and contact portions of a proximal humerus and a humeral shaft, the bone plate having a body portion, a neck portion, and a first end portion, the body portion including a first end, a second end opposite the first end, a longitudinal axis extending between the first and second ends, a plurality of bone screw receiving apertures adapted to overlie the humeral shaft, and a first contact surface adjacent the second end and adapted to contact the exterior surface of the humeral shaft, the longitudinal axis of the body portion being adapted to be substantially aligned with the humeral shaft when the bone plate is attached to the humerus, and the plurality of bone screw receiving apertures being positioned from adjacent a midpoint of and the second end of the body portion, the neck portion extending from between the first and second ends of the body portion, the neck portion being adapted to bridge the biceps groove of the proximal humerus when the bone plate is attached to the humerus, the neck portion terminating in the first end portion, the first end portion including a second contact surface adapted to contact the exterior surface of the lesser tuberosity of the proximal humerus, and at least two bone screw receiving apertures adapted to overlie the lesser tuberosity, the at least two bone screw receiving apertures each including an axis, the axes of the at least two bone receiving apertures being oriented away from the articular surface of the proximal humerus when the bone plate is attached to the humerus; at least a first set of bone screws, a first bone screw of the first set of bone screws being received through a first of the plurality of bone screw receiving apertures and into the humeral shaft, and a second bone screw of the first set of bone screws being received through a second of the plurality of bone screw receiving apertures and into the humeral shaft, the first and second bone screws of the first set of bone screws facilitating attached of the bone portion to the humeral shaft; and at least a second set of bone screws, each bone screw of the at least a second set of bone screws having a longitudinal axis, a first bone screw of the second set of bone screws being received through a first of the at least two bone screw receiving apertures and into the lessor tuberosity, a second bone screw of the second set of bone screws being received through a second of the at least two bone screw receiving apertures and into the lessor tuberosity, the longitudinal axes of the first and second bone screws of the second set of bone screws being aligned with the axes of the first and second bone screw receiving apertures and being oriented away from the articular surface of the proximal humerus when the bone plate is attached to the humerus.

It is understood that both the foregoing general description and the following detailed description are exemplary and exemplary only, and are not restrictive of the invention as claimed.

BRIEF DESCRIPTION OF THE DRAWINGS

The accompanying drawings, which are incorporated in and constitute a part of the specification, illustrate preferred embodiments of the invention. Together with the description, they serve to explain the objects, advantages and principles of the invention. In the drawings.

DETAILED DESCRIPTION OF THE PREFERRED EMBODIMENT

The following description is intended to be representative only and not limiting, and many variations can be anticipated according to these teachings. Reference will now be made in detail to the preferred embodiments of this invention, examples of which are illustrated in the accompanying drawings.

Figure 1:
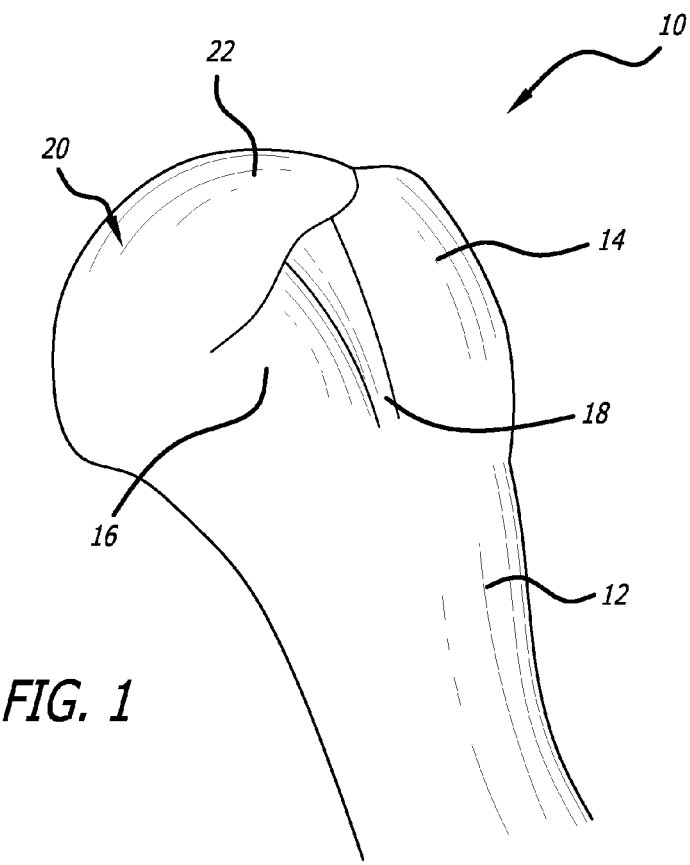
FIG. 1 is a perspective view of a left proximal humerus.
Figure 2:
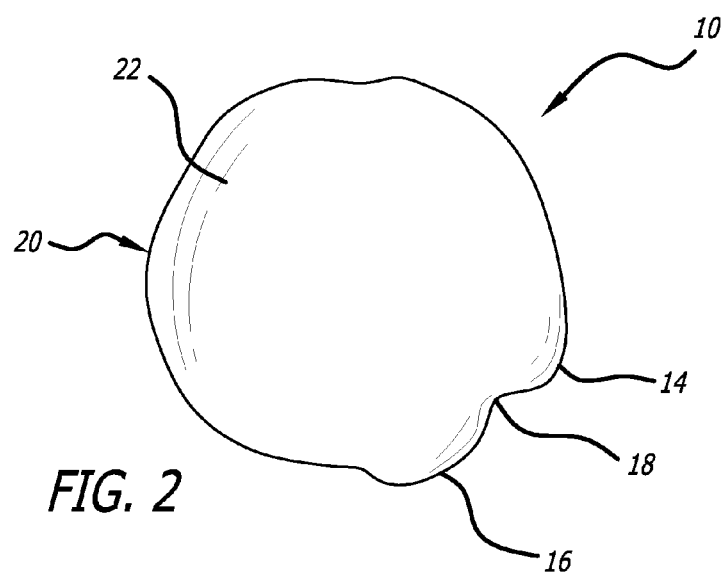
FIG. 2 is a top view of the left proximal humerus depicted in FIG. 1.

FIGS. 1 and 2 depict the portions of a left proximal humerus generally indicated by the numeral 10. Proximal humerus 10 is joined to humeral shaft 12 (FIG. 1), and includes greater tuberosity 14, lesser tuberosity 16, biceps groove 18, humeral head 20, and an articular surface 22 of humeral head 20. Biceps groove 18 is disposed between greater tuberosity 14 and lesser tuberosity 16. Thus, as depicted in FIG. 2, greater tuberosity 14 is disposed laterally of biceps groove 18, and lesser tuberosity 16 is disposed medially of biceps groove 18. Furthermore, in FIGS. 3-5A, lesser tuberosity 16 is partially covered by the fixation devices of the present invention. Thus, the lead line associated with numeral 16 in FIGS. 3-5A points to proximal humerus 10 adjacent where fixation devices of the present invention are positioned.

As discussed above, to facilitate fracture fixation and fracture reduction, a bone plate typically has been attached to greater tuberosity 14. However, the placement of bone screws by the bone plate attached solely to greater tuberosity 14 is less than optimal. The bone screws will likely be disposed at a significantly perpendicular angle with respect to articular surface 22 of humeral head 20, and thus, cause a significant incidence of penetration of articular surface 22.

Figure 3:
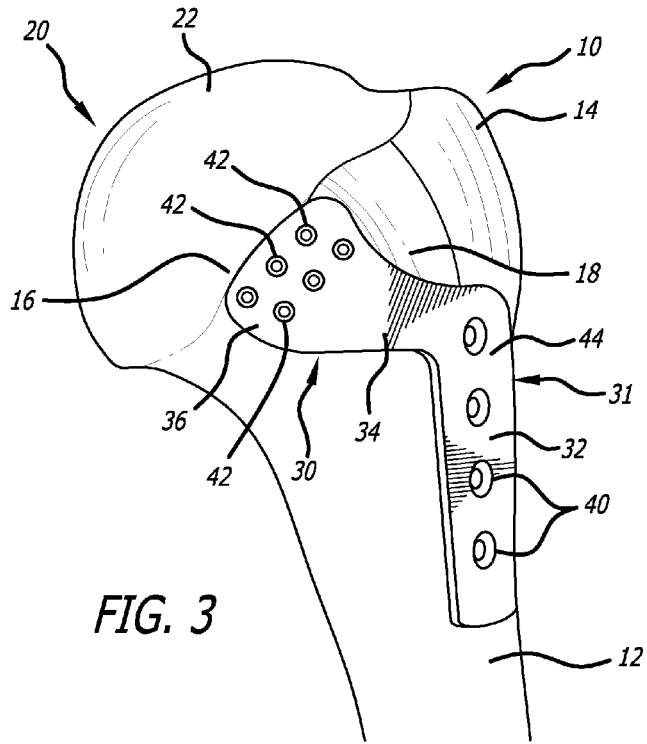
FIG. 3 is a perspective view of a bone plate of a first embodiment of a fixation device according to the present invention positioned with respect to the proximal humerus.
Figure 3A:
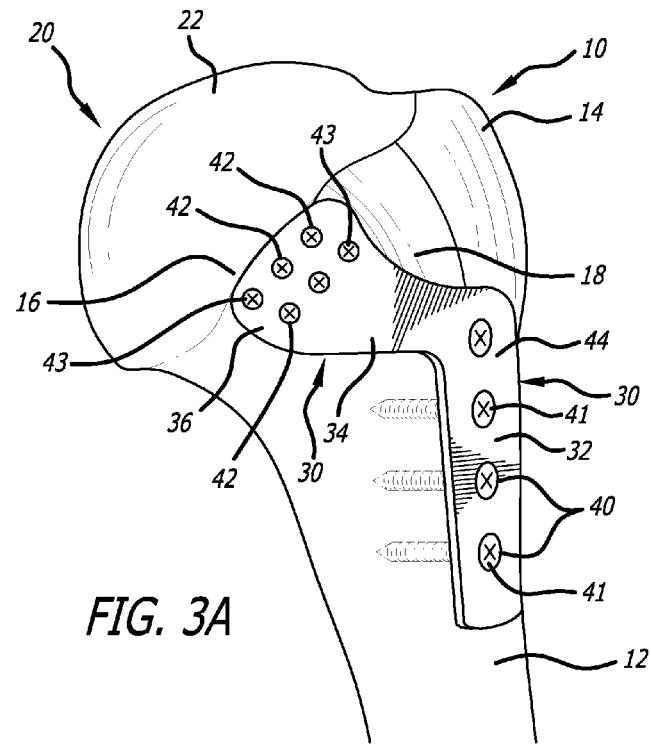
FIG. 3A is a perspective view of the fixation device of FIG. 3 depicting the placement of bone screws used in the fixation device.

A first embodiment of a fixation device according to the present invention is generally indicated by the numeral 30 in FIGS. 3 and 3A. Fixation device 30 includes a "dogleg-shaped" bone plate 31 and various bone screws inserted therethrough and into bone.

Bone plate 31 has a body portion 32, a neck portion 34, and an end portion 36. Body portion 32 includes apertures 40 spaced therealong, and is attached to humeral shaft 12 and portions of proximal humerus 10 using bone screws 41 (FIG. 3A) inserted through apertures 40 and into the bone. As depicted in FIGS. 3 and 3A, neck portion 34 extends from body portion 32 over biceps groove 18, and terminates at end portion 36. End portion 36 includes apertures 42 spaced apart thereon, and is attached to lesser tuberosity 16 using bone screws 43 (FIG. 3A) inserted through apertures 42 and into proximal humerus 10. Apertures 40 and 42 extend between an upper surface 44 and a lower surface (not shown) of bone plate 31. The lower surface of bone plate 31 can be contoured according to the surfaces of proximal humerus 10 to provide a flush interface therebetween.

Apertures 42 each include an axis substantially perpendicular to at least one of the upper and lower surfaces of bone plate 31 adjacent thereto, and the longitudinal axes of bone screws 43 received therein are ultimately aligned with the axes of apertures 42. The angles of the longitudinal axis of apertures 42 serve to orient bone screws 43 in positions that inhibit the incidence of penetration thereof through articular surface 22. For example, the orientation angles afforded by apertures 42 serve to position bone screws 43 in at least substantially tangential orientations with respect to articular surface 22 of humeral head 20. Accordingly, the axes of apertures 42 and the longitudinal axes of bone screws 43 received therein can be oriented away from and avoid intersection with articular surface 22, thereby decreasing the incidence of penetration of bone screws 43 through articular surface 22, while also preventing a loss of fracture fixation and fracture reduction.

Figure 4:
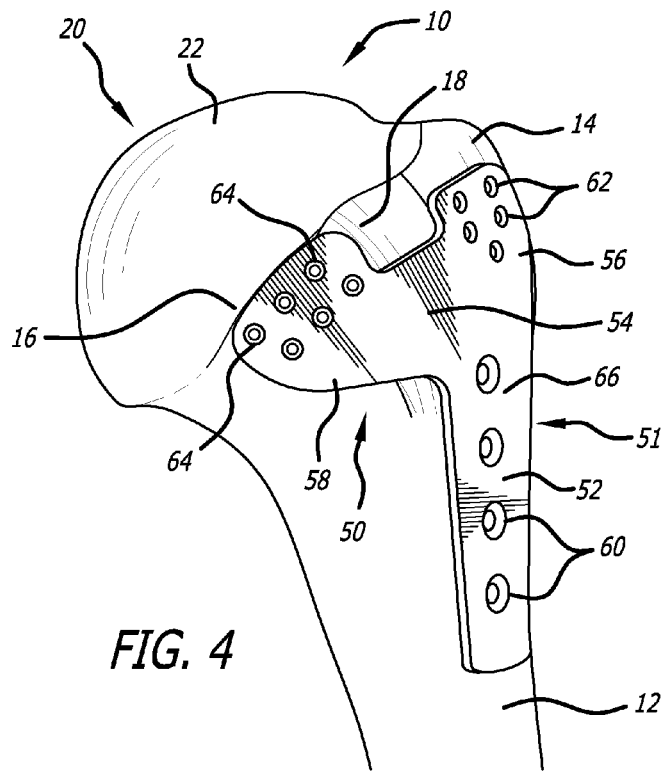
FIG. 4 is a perspective view of a bone plate of a second embodiment of a fixation device according to the present invention positioned with respect to the proximal humerus.
Figure 4A:
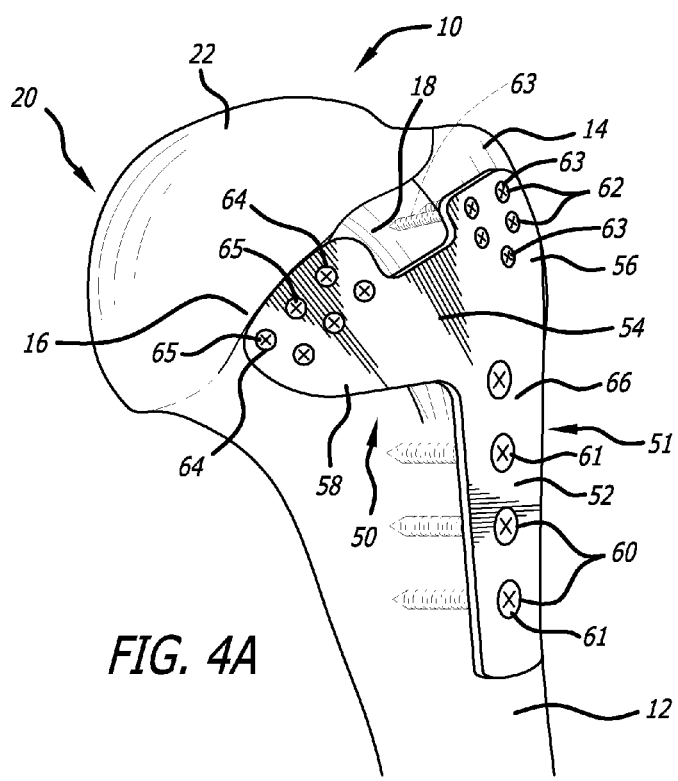
FIG. 4A is a perspective view of the fixation device of FIG. 4 depicting the placement of bone screws used in the fixation device.

A second embodiment of a fixation device according to the present invention is generally indicated by the numeral 50 in FIGS. 4 and 4A Fixation device 50 includes an "h-shaped" bone plate 51 and various screws inserted therethrough and into bone.

Bone plate 51 has a body portion 52, a neck portion 54, a first end portion 56, and a second end portion 58. Body portion 52 includes apertures 60 spaced therealong, and is attached to humeral shaft 12 and portions of proximal humerus 10 using bone screws 61 (FIG. 4A) inserted through apertures 60 and into the bone. As depicted in FIGS. 4 and 4A, first end portion 56 is contiguous with body portion 52, and includes apertures 62 spaced apart thereon. First end portion 56 is attached to greater tuberosity 14 using bone screws 63 (FIG. 4A) inserted through apertures 62 and into proximal humerus 10. As depicted in FIGS. 4 and 4A, neck portion 54 extends from between body portion 52 and first end portion 56 over biceps groove 18, and terminates at second end portion 58. Second end portion 58 includes apertures 64 spaced apart thereon, and is attached to lesser tuberosity 16 using bone screws 65 (FIG. 4A) inserted through apertures 64 and into proximal humerus 10. Apertures 60, 62, and 64 extend between an upper surface 66 and a lower surface (not shown) of bone plate 51. The lower surface of bone plate 51 can be contoured according to the surfaces of proximal humerus 10 to provide a flush interface therebetween.

Apertures 62 each include an axis substantially perpendicular to at least one of the upper and lower surfaces of bone plate 51 adjacent thereto, and the longitudinal axes of bone screws 63 received therein are ultimately aligned with the axes of apertures 62. As discussed below, use of second end portion 58 to facilitate attachment of bone plate 51 to proximal humerus 10 affords use of shorter bone screws 63 in apertures 62 than those typically used to secure attachment to greater tuberosity 14.

Like apertures 62, apertures 64 each include an axis substantially perpendicular to at least one of the upper and lower surfaces of bone plate 51 adjacent thereto, and the longitudinal axes of bone screws 65 received therein are ultimately aligned with the axes of apertures 64. The angles of the axes of apertures 64 serve to orient bone screws 65 in positions that inhibit the incidence of penetration thereof through articular surface 22. For example, the orientation angles afforded by apertures 64 serve to position bone screws 65 in at least substantially tangential orientations with respect to articular surface 22 of humeral head 20. As such, the axes of apertures 64 and the longitudinal axes of bone screws 65 received therein can be oriented away from and avoid intersection with articular surface 22. Accordingly, such an orientation allows bone screws 63 inserted into lesser tuberosity 16 to share (with bone screws 63) in resisting the joint forces applied in a direction perpendicular to articular surface 22, thereby decreasing the incidence of penetration of bone screws 63 through articular surface 22, while also increasing the overall mechanical strength of the connection, preventing a loss of fracture fixation and fracture reduction.

Because bone plate 51 is attached using (1) first end portion 56 to greater tuberosity 14, and (2) using second end portion 58 to lesser tuberosity 16, bone screws 63 used with apertures 62 can be shorter than those typically used to attach a bone plate solely to greater tuberosity 14. Thus, given that shorter bone screws 63 are used, the incidence of shorter bone screws 63 (inserted through greater tuberosity 14) penetrating articular surface 22 of humeral head 20 can be significantly lessened. That is, even if the orientations of the axes of apertures 62 and the longitudinal axes of bone screws 63 received therein intersect articular surface 22, the lengths of bone screws 63 received in apertures 62 do not afford penetration of articular surface 22.

Figure 5:
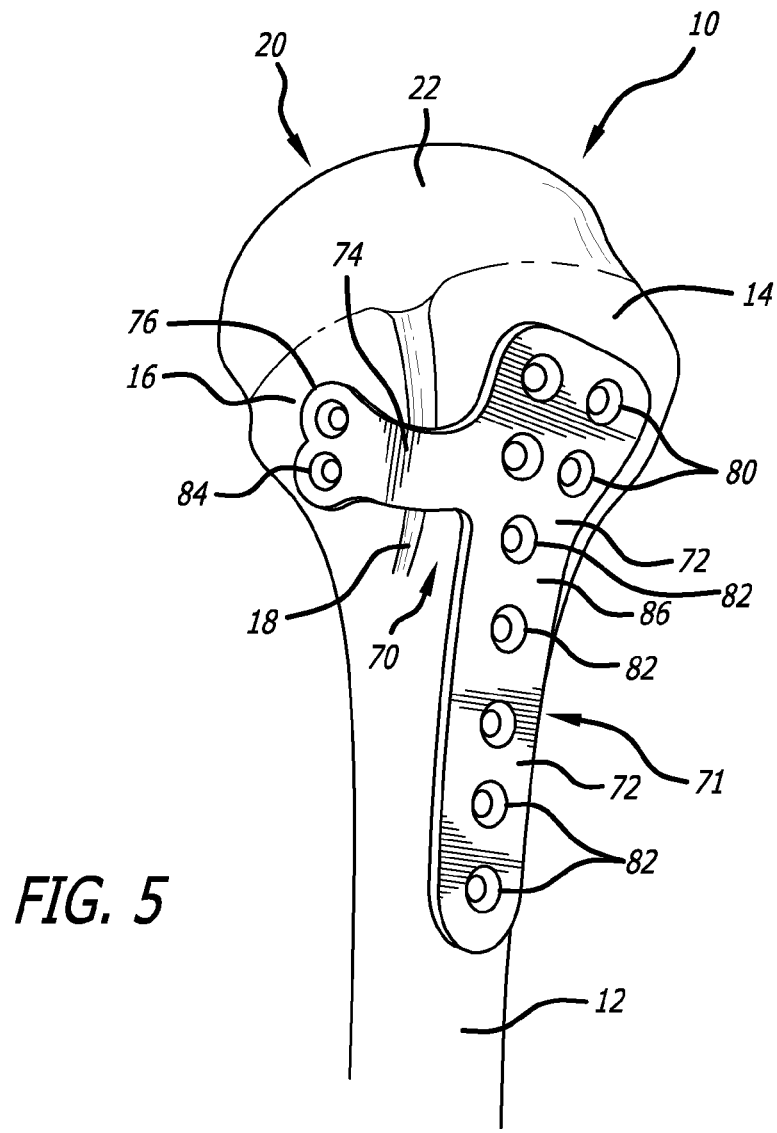
FIG. 5 is a perspective view of a bone plate of a third embodiment of a fixation device according to the present invention positioned with respect to the proximal humerus.
Figure 5A:
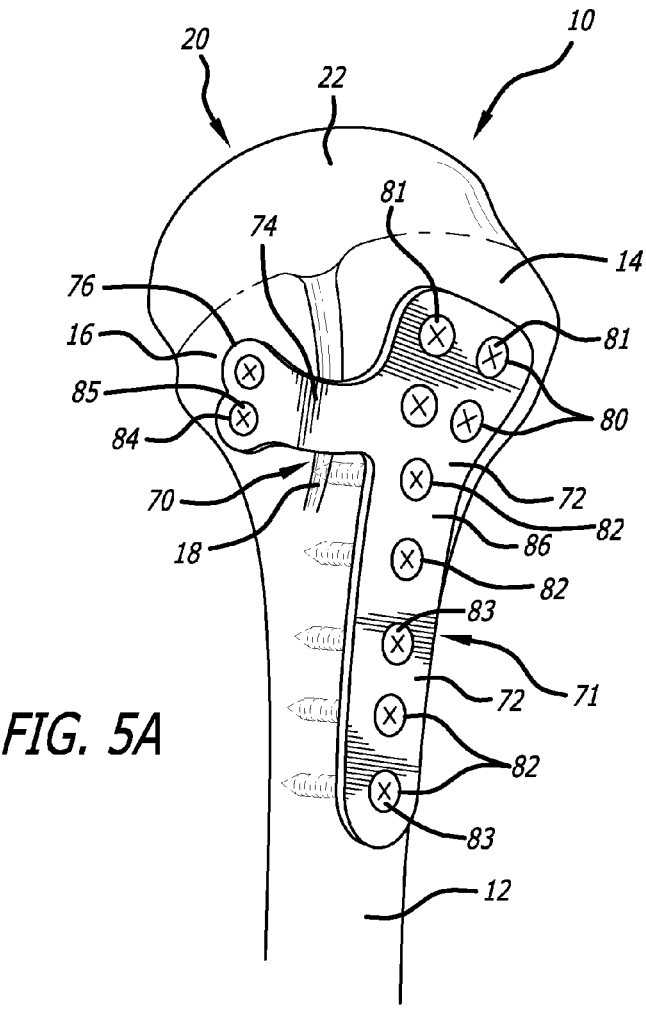
FIG. 5A is a perspective view of the fixation device of FIG. 5 depicting the placement of bone screws used in the fixation device.
Figure 6:
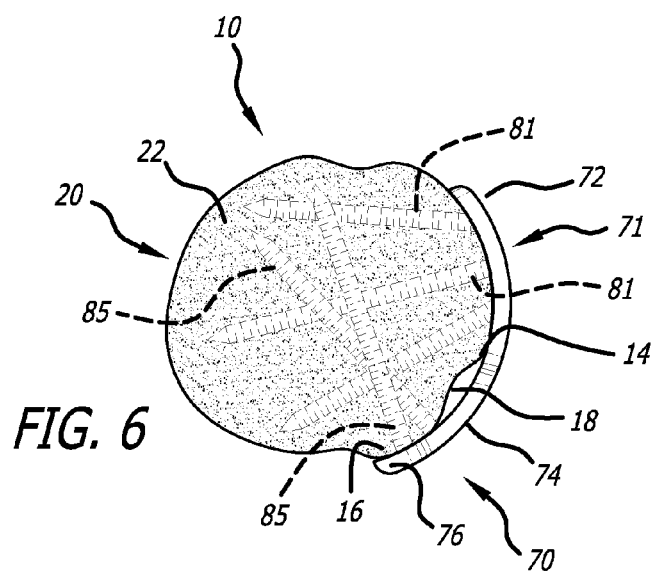
FIG. 6 is a top cross-sectional view of the fixation device depicted in FIG. 5A taken through the greater tuberosity, the lesser tuberosity, and a portion of the fixation device.

A third embodiment of a fixation device according to the present invention is generally indicated by the numeral 70 in FIGS. 5, 5A, and 6. Fixation device 70 includes a "y-shaped" bone plate 71 and various screws inserted therethrough and into bone.

Bone plate 71 has a body portion 72, a neck portion 74, and an end portion 76. As depicted in FIGS. 5 and 5A, body portion 72 extends along greater tuberosity 14 and humeral shaft 12. Body portion 72 includes first apertures 80 and second apertures 82 formed therein. First apertures 80 are spaced apart from one another at one end of body portion 72 (ultimately adjacent greater tuberosity 14), and second apertures 82 are spaced along body portion 72 from adjacent first apertures 80 to the other end of body portion 72 (ultimately adjacent humeral shaft 12).

Furthermore, as depicted in FIG. 5, neck portion 74 extends from body portion 72 over biceps groove 18, and terminates at end portion 76. Neck portion 74 can be formed integrally with body portion 72 (as depicted in FIG. 5), or neck portion 74 can be formed separately from body portion 72. When body portion 72 and neck portion 74 are formed separately, body portion 72 and neck portion 74 can be attached to one another before or during surgery. Furthermore, neck portion 74 can be positioned to overlap body portion 72, and then body portion 72 and neck portion 74 can be attached to one another; or body portion 72 can be positioned to overlap neck portion 74, and then body portion 72 and neck portion 74 can be attached to one another.

When formed separately from one another, body portion 72 and neck portion 74 can be attached to one another using one or more fasteners such as screws (not shown). Furthermore, to facilitate attachment of one another, body portion 72 and neck portion 74 can each include one or more corresponding apertures (not shown) formed therein and configured to receive the associated fastener or fasteners. Accordingly, during surgery, body portion 72, for example, can be attached to proximal humerus 10 first, and then neck portion can 74 can be attached to proximal humerus 10 and body portion 72, or neck portion 74 can attached to proximal humerus 10 first, and then body portion 72 can be attached to proximal humerus 10 and neck portion 74.

End portion 76 includes apertures 84 spaced apart from one another thereon (ultimately adjacent lesser tuberosity 16). Apertures 80, 82, and 84 extend between an upper surface 86 and a lower surface (not shown) of the bone plate 71. The lower surface of bone plate 71 can be contoured according to the surfaces of proximal humerus 10 to provide a flush interface therebetween.

First apertures 80 are configured to receive bone screws 81 (FIGS. 5A and 6) and second apertures 82 are configured to receive bone screws 83 (FIG. 5A) to facilitate attachment of body portion 72 to greater tuberosity 14 and humeral shaft 12, respectively. Furthermore, apertures 84 are configured to receive bone screws 85 (FIG. 5A and 6) therethrough to attach end portion 76 to lesser tuberosity 16.

Apertures 80 each include an axis substantially perpendicular to at least one of upper and lower surfaces of bone plate 71 adjacent thereto, and the longitudinal axes of bone screws 81 received therein are ultimately aligned with the axes of apertures 80. As discussed below, use of end portion 76 to facilitate attachment of bone plate 71 to proximal humerus 10 affords use of shorter bone screws 81 in apertures 80 than those typically used to secure attachment to greater tuberosity 14.

Like apertures 80, apertures 84 each include an axis substantially perpendicular to at least one of the upper and lower surfaces of bone plate 71 adjacent thereto, and the longitudinal axes of bone screws 85 received therein are ultimately aligned with the axes of apertures 84. The angles of the axes of apertures 84 serve to orient bone screws 85 in positions that inhibit the incidence of penetration thereof through articular surface 22. For example, the orientation angles afforded by apertures 84 serve to position bone screws 85 in at least substantially tangential orientations with respect to articular surface 22 of humeral head 20. As such, the axes of apertures 84 and the longitudinal axes of bone screws 85 received therein can be oriented away from and avoid intersection with articular surface 22, and are substantially perpendicular to the longitudinal axes of bone screws 81. Accordingly, such an orientation allows bone screws 85 to share (with bone screws 81) in resisting the joint forces applied in a direction perpendicular to articular surface 22, thereby decreasing the incidence of penetration of bone screws 85 through articular surface 22, while also increasing the overall mechanical strength of the connection, preventing a loss of fracture fixation and fracture reduction. Furthermore, as discussed below, the right angle construct formed by the substantial perpendicularity between the longitudinal axes of bone screws 81 and 85 provides significant mechanical advantages.

Because the bone plate 71 is attached using (1) apertures 80 and bone screws 81 to greater tuberosity 14, and (2) using apertures 84 (of end portion 76) and bone screws 85 to lesser tuberosity 16, bone screws 81 can be shorter than those typically used to attach a bone plate solely to greater tuberosity 14. Thus, given that bone screws 81 are shorter than those typically used, the incidence of bone screws 81 (inserted through greater tuberosity 14) penetrating articular surface 22 of humeral head 20 can be significantly lessoned. That is, even if the orientations of the axes of apertures 80 and the longitudinal axes of bone screws 81 received therein intersect articular surface 22, the lengths of bone screws 81 received in apertures 80 do not afford penetration of articular surface 22.

The right angle construct formed by the substantial perpendicularity between the longitudinal axes of bone screws 81 and 85 provides significant mechanical advantages that reinforce the connection between proximal humerus 10 and bone plate 71. That is, in addition to affording shorter bone screws 81, the substantial perpendicularity between the longitudinal axes of bone screws 81 and 85 serves in stabilizing proximal humerus 10.

To further stabilize proximal humerus 10, bone screws 81 and 85 can be configured to engage one another within proximal humerus 10. For example, bone screws 85 inserted into lesser tuberosity 16 (via end portion 76) can engage bone screws 81 inserted into greater tuberosity 14 (via body portion 72). Bone screws 85 can impinge on bone screws 81, or bone screw 81 can include apertures (not shown) for receiving bone screws 85. Either way, the engagement of bone screws 81 and 85 forms a lattice structure within proximal humerus 10. In doing so, bone screws 81 and 85 strengthen proximal humerus 10, and further prevent a loss of fracture fixation and fracture reduction thereof. The structure and formation of lattice structures (such as that form by bone screws 81 and 85) is described in pending U.S. application Ser. Nos. 11/050,304 and 13/253,564, which are herein incorporated by reference.

Other embodiments of the invention will be apparent to those skilled in the art from consideration of the specification and practice of the invention disclosed herein. Accordingly, it is intended that the specification and examples be considered as exemplary only.

I claim:

1. A fixation device for facilitating reductions and repair of a fractured humerus, the humerus including at least a proximal humerus, a humeral shaft, a humeral head, a biceps groove, a lesser tuberosity, a greater tuberosity, and an articular surface, the fixation device comprising:

a bone plate configured to overlie and contact portions of the proximal humerus and the humeral shaft, said bone plate including a body portion and a first neck portion, said body portion having a proximal end configured to be placed proximate the humeral head, and a distal end opposite said proximal end, said body portion defining a first mid-longitudinal axis extending through said proximal end and said distal end thereof, and said body portion having a maximum width perpendicular to the first mid-longitudinal axis thereof, said first neck portion extending from said proximal end of said body portion, said first neck portion defining a second mid-longitudinal axis generally transverse to the first mid-longitudinal axis, said first neck portion having a first portion connected to said proximal end of said body portion, and said first neck portion having a second portion terminating in a first end portion of said bone plate, the second mid-longitudinal axis extending through said first portion of said first neck portion, and through said first end portion of said bone plate;

said body portion including a plurality of bone screw receiving apertures configured to overlie the humeral shaft, and a first contact surface configured to contact the exterior surface of the humeral shaft, the first mid-longitudinal axis of said body portion being configured to be substantially aligned with the humeral shaft when said bone plate is attached to the humerus;

said first neck portion being configured to bridge the biceps groove of the proximal humerus when said bone plate is attached to the humerus, said first end portion including a second contact surface configured to contact the exterior surface of the lesser tuberosity of the proximal humerus, and said second portion of said first neck portion including at least two bone screw receiving apertures configured to overlie the lesser tuberosity, said at least two bone screw receiving apertures each including an axis, the axes of said at least two bone screw receiving apertures being oriented away from the articular surface of the proximal humerus when said bone plate is attached to the humerus;

at least a first set of bone screws, a first bone screw of said first set of bone screws configured to be received through a first of said plurality of bone screw receiving apertures and into the humeral shaft, and a second bone screw of said first set of bone screws configured to be received through a second of said plurality of bone screw receiving apertures and into the humeral shaft, said first and second bone screws of said first set of bone screws facilitating attachment of said bone portion to the humeral shaft; and at least a second set of bone screws, each bone screw of said at least a second set of bone screws having a longitudinal axis, a first bone screw of said second set of bone screws configured to be received through a first of said at least two bone screw receiving apertures and into the lessor tuberosity, a second bone screw of said second set of bone screws configured to be received through a second of said at least two bone screw receiving apertures and into the lessor tuberosity, the longitudinal axes of said first and second bone screws of said second set of bone screws being aligned with the axes of said first and second bone screw receiving apertures and being oriented away from the articular surface of said proximal humerus when said bone plate is attached to the humerus;

wherein said first neck portion has a first side and a second side, said first portion of said first neck portion has a first width between said first and second sides, said first width being adjacent said body portion and perpendicular to the second mid-longitudinal axis, and said second portion of said first neck portion has a second width and a third width between said first and second sides, said second width being adjacent said first end portion and between said first end portion and said at least two bone screw receiving apertures of said second portion of said first neck portion, said second width being perpendicular to the second mid-longitudinal axis, said second width being greater than said first width, said third width, and said maximum width of said body portion, said second portion being continuous across said third width between said first and second sides.

2. The fixation device of claim 1, wherein said bone plate includes a second neck portion extending from said body portion and terminating in a second end portion, said second end portion being spaced apart from said first end portion, said second end portion including a third contact surface configured to contact the exterior surface of the greater tuberosity of the proximal humerus, and at least two bone screw receiving apertures configured to overlie the greater tuberosity.

3. The fixation device of claim 2, further comprising at least a third set of bone screws, a first bone screw of said third set of bone screws configured to be received through a first bone screw receiving hole of said at least two bone screw receiving holes overlying the greater tuberosity and into the greater tuberosity, and a second bone screw of said third set of bone screws configured to be received through a second bone screw receiving hole of said at least two bone screw receiving holes overlying the greater tuberosity and into the greater tuberosity.

4. The fixation device of claim 3, wherein the lengths of each bone screw of said third set of bone screws do not afford penetration of the articular surface of the proximal humerus.

5. The fixation device of claim 1, wherein said body portion and said first neck portion are substantially perpendicular to one another.

6. The fixation device of claim 1, wherein at least said first bone screw of said second set of bone screws, and at least said second bone screw of said second set of bone screws are oriented to define a lattice structure.

7. The fixation device of claim 1, wherein the width of said first neck portion increases gradually from said first width to said second width.

8. The fixation device claim 2, wherein a shape of the bone plate substantially defines an upside-down lower-case letter h.

9. The fixation device claim 2, wherein a shape of the bone plate substantially defines a lower-case letter y.

10. A fixation device for facilitating reductions and repair of a fractured humerus, the humerus including at least a proximal humerus, a humeral shaft, a biceps groove, a lesser tuberosity, a greater tuberosity, and an articular surface, the fixation device comprising:

a bone plate configured to overlie and contact portions of the proximal humerus and the humeral shaft, said bone plate including a body portion and at least one neck portion, said body portion having a proximal end configured to be placed proximate the humeral head, and a distal end opposite said proximal end, said body portion defining a first mid-longitudinal axis extending through said proximal end and said distal end thereof, and said body portion having a maximum width perpendicular to the first mid-longitudinal axis thereof, said at least one neck portion extending from said proximal end of said body portion, said at least one neck portion defining a second mid-longitudinal axis generally transverse to said first mid-longitudinal axis, said at least one neck portion terminating in an end portion, the second mid-longitudinal axis extending through said end portion of said at least one neck portion and said proximal end of said body portion, said at least one neck portion having a first side and a second side, said at least one neck portion having a first width between said first and second sides and proximate said proximal end of said body portion, and said at least one neck portion having a second width and a third width between said first and second sides and proximate said end portion, said first width, said second width, and said third width being perpendicular to the second mid-longitudinal axis, said second width being greater than said first width, said third width, and said maximum width of said body portion, said at least one neck portion being continuous across said third width between said first and second sides;

said body portion including a plurality of bone screw receiving apertures configured to overlie the humeral shaft, and a first contact surface adjacent said distal end and configured to contact the exterior surface of the humeral shaft, the first mid-longitudinal axis of said body portion being configured to be substantially aligned with the humeral shaft when said bone plate is attached to the humerus, and said plurality of bone screw receiving apertures being positioned from adjacent a midpoint of to adjacent said distal end of said body portion;

said at least one neck portion being configured to bridge the biceps groove of the proximal humerus when said bone plate is attached to the humerus, said end portion including a second contact surface configured to contact the exterior surface of the lesser tuberosity of the proximal humerus, and said at least one neck portion adjacent said end portion including at least two bone screw receiving apertures configured to overlie the lesser tuberosity, said second width of said at least one neck portion being positioned between said at least two bone screw receiving apertures and said end portion, said at least two bone screw receiving apertures each including an axis, the axes of said at least two bone screw receiving apertures being oriented away from the articular surface of the proximal humerus when said bone plate is attached to the humerus;

at least a first set of bone screws, a first bone screw of said first set of bone screws configured to be received through a first of said plurality of bone screw receiving apertures and into the humeral shaft, and a second bone screw of said first set of bone screws configured to be received through a second of said plurality of bone screw receiving apertures and into the humeral shaft, said first and second bone screws of said first set of bone screws facilitating attachment of said bone plate to the humeral shaft; and at least a second set of bone screws, each bone screw of said at least a second set of bone screws having a longitudinal axis, a first bone screw of said second set of bone screws configured to be received through a first of said at least two bone screw receiving apertures and into the lessor tuberosity, a second bone screw of said second set of bone screws configured to be received through a second of said at least two bone screw receiving apertures and into the lessor tuberosity, the longitudinal axes of said first and second bone screws of said second set of bone screws being aligned with the axes of said first and second bone screw receiving apertures and being oriented away from the articular surface of said proximal humerus when said bone plate is attached to the humerus;

wherein the width of said at least one neck portion gradually widens from said first width to said second width.

11. The fixation device of claim 10, wherein, when said bone plate is attached to the humerus, said proximal end of said body portion is positioned adjacent said greater tuberosity.

12. The fixation device of claim 11, wherein said body portion includes a third contact surface adjacent said proximal end and configured to contact the exterior surface of the greater tuberosity of the proximal humerus, and at least two bone screw receiving apertures configured to overlie the greater tuberosity.

13. The fixation device of claim 12, further comprising at least a third set of bone screws, a first bone screw of said third set of bone screws configured to be received through a first bone screw receiving hole of said at least two bone screw receiving holes overlying the greater tuberosity and into the greater tuberosity, and a second bone screw of said third set of bone screws configured to be received through a second bone screw receiving hole of said at least two bone screw receiving holes overlying the greater tuberosity and into the greater tuberosity.

14. The fixation device of claim 13, wherein the lengths of each bone screw of said third set of bone screws do not afford penetration of the articular surface of the proximal humerus.

\* \* \* \* \*

UNITED STATES PATENT AND TRADEMARK OFFICE
CERTIFICATE OF CORRECTION

PATENT NO.         : 9,254,154 B2
APPLICATION NO.    : 13/412039
DATED              : February 9, 2016
INVENTOR(S)        : Eduardo Gonzalez-Hernandez It is certified that error appears in the above-identified patent and that said Letters Patent is hereby corrected as shown below:

<u>Title Page 3, Item (56) References Cited, Other Publications</u>:
Column 2, line 51: change "laod" to -- load --;
Column 2, line 53: change "2008" to -- 2009 --;
Column 2, line 58: change "M.V." to -- M.B. --;
Column 2, line 59: change "intial" to -- initial --;
Column 2, line 60: change "fixiation" to -- fixation --;
Column 2, line 61: after "Periarticular" insert -- Proximal --;
Column 2, line 69: change "Looking" to -- Locking --; and
Column 2, line 70: change "vol. 39" to -- vol. 89 --.

Signed and Sealed this
Nineteenth Day of July, 2016

Michelle K. Lee
*Director of the United States Patent and Trademark Office*